(12) United States Patent
von Doehren et al.

(10) Patent No.: US 8,147,690 B2
(45) Date of Patent: Apr. 3, 2012

(54) CHROMATOGRAPHY COLUMN

(75) Inventors: Norwin Rolf Leonhard von Doehren, Bergen op Zoom (NL); Menno Heringa, Middelburg (NL); Pieter Johannes van Keulen, Koudekerke (NL); Wilroy E. Bennen, Vlissingen (NL)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 12/909,311

(22) Filed: Oct. 21, 2010

(65) Prior Publication Data
US 2011/0094953 A1 Apr. 28, 2011

(30) Foreign Application Priority Data
Oct. 23, 2009 (EP) .................................... 09013435

(51) Int. Cl.
*B01D 15/08* (2006.01)

(52) U.S. Cl. ..................................... 210/198.2; 210/656

(58) Field of Classification Search .................. 210/656, 210/659, 198.2, 232, 450; 96/101, 106
See application file for complete search history.

(56) References Cited

U.S. PATENT DOCUMENTS

| | | | |
|---|---|---|---|
| 4,457,846 A * | 7/1984 | Munk | 210/656 |
| 4,469,597 A * | 9/1984 | Mott | 210/198.2 |
| 4,882,047 A | 11/1989 | Shalon | |
| 5,342,515 A * | 8/1994 | Radmacher | 210/198.2 |
| 5,714,074 A * | 2/1998 | Karlsson et al. | 210/656 |
| 6,267,884 B1 | 7/2001 | Myers | |
| 6,387,256 B1 | 5/2002 | Tuvim | |
| 6,527,951 B1 | 3/2003 | Tuvim | |
| 7,125,489 B2 | 10/2006 | Zelechonok et al. | |
| 7,588,683 B2 * | 9/2009 | Willis et al. | 210/198.2 |
| 2007/0175809 A1 | 8/2007 | Cao et al. | |
| 2010/0126921 A1 * | 5/2010 | Rahn et al. | 210/198.2 |
| 2011/0094953 A1 * | 4/2011 | Doehren et al. | 210/198.2 |

* cited by examiner

*Primary Examiner* — Ernest G Therkorn

(57) ABSTRACT

A chromatography column includes a tube, a frit assembly, a first end fitting and a second end fitting. An annular protrusion extends from an end face of the tube to a protrusion height and circumscribes a chamber in fluid communication with the axial bore. Both the chamber and the bore may be filled with a packing material. The frit assembly includes a deformable ring having a yield strength less than a yield strength of the annular protrusion. The ring contacts the annular protrusion such that the frit assembly provides a chamber boundary that retains the packing material. The first end fitting is securely fastened to the tube such that the ring is axially compressed and deformed around the annular protrusion, the chamber height is less than the protrusion height, and the packing material is compressed.

13 Claims, 4 Drawing Sheets

CHROMATOGRAPHY COLUMN

PRIORITY CLAIM

This application claims the benefit of European Patent Application Serial No. 09013435.4, filed Oct. 23, 2009, titled "CHROMATOGRAPHY COLUMN", the content of which is incorporated by reference herein in its entirety.

FIELD OF THE INVENTION

The present invention relates generally to the design, assembly and use of columns utilized for analytical separation in the field of liquid chromatography.

BACKGROUND OF THE INVENTION

Liquid chromatography (LC) is a technique for performing an analytical separation of a sample into constituent components, i.e., the analytes of interest to a researcher. As readily known by persons skilled in the art, during the course of a chromatographic separation, the sample is transported in a mobile phase (or solvent), which is a liquid in LC techniques. The mobile phase is forced through a stationary phase that is immiscible relative to the mobile phase. Typically, the stationary phase is provided in the form of a volume of particles (a column packing bed) supported in a column or cartridge through which the sample and mobile phase flow. The column packing bed is typically retained at each end of the column by a frit or filter that allows the mobile phase and sample to flow through while preventing the packing material from escaping the column. The frits are typically secured in place by end fittings located at the column inlet end and outlet end, respectively. The inlet end of the column is connected to an inlet conduit by which the sample/mobile phase is introduced into the column. A mobile phase reservoir, pump and sample injector are located upstream and interconnected to the column inlet via the inlet conduit. The outlet end of the column is connected via an outlet conduit to a suitable detector, which may operate based on ultraviolet or visible light absorbance, conductivity, fluorescence, light scattering, mass resolution, etc. In the column, the respective compositions of the mobile phase and stationary phase are selected to cause the analytes of the sample to become distributed between the mobile phase and stationary phase to varying degrees dependent on the nature of the respective analytes. Analytes that are strongly retained by the stationary phase travel slowly with the mobile phase, while analytes that are weakly retained by the stationary phase travel more rapidly. As a result, analytes of differing compositions become separated from each other as the mobile phase flows through the column. In this manner, the analytes are in effect sorted sequentially as the eluent flows out from the column, thereby facilitating their analysis by the detector.

The mechanical separation power or efficiency of a chromatography column depends in part on the physical attributes of the packing bed (stationary phase). To realize acceptable efficiency and resolution, the packing bed must be stable and uniformly packed. Dead spaces or voids within the packing material, or more generally reduced particle density, result in peak broadening and/or peak tailing observed in the acquired data and consequently loss of potentially valuable analytical information. Loss of stability or uniformity in the packing material may be caused by a number of factors, such as a poorly designed column packing process, a subsequent column assembly step that allows the density of the packing bed to be reduced, or subsequent use of the column in which the high-pressure fluid flow required for the LC technique destabilizes the packing bed.

The problem of providing a uniform, stable packing bed has been addressed in a few ways. In PCT App. Pub. No. WO 2004/024285, an LC column is taught in which a preformed filter assembly at the inlet end has a filter that includes a protruding portion. When the filter assembly is installed, the filter protrudes into the interior of the column where the packing bed is located to attain some compression of the packing bed. In UK Patent App. Pub. No. GB 2 429 939, an LC column is taught in which a metal filter is press-fitted into the open end of the column tube. Upon installation of an end fitting of the column, a metal compression body bears against the end of the tube of the column, which deforms the end of the tube. As the end of the tube yields in this manner, the compression body contacts the filter and causes the filter to bear against the packing bed to attain compression thereof.

In view of the foregoing, there is a need for providing chromatographic column hardware configured for improved longevity, mechanical stability and performance of the packing bed. There is also a need for providing a chromatographic column configured for uniformly compressing the packing bed contained in the column to a desired density level, and maintaining the uniformity of the density and stability of the packing bed during high-pressure chromatography operations.

SUMMARY OF THE INVENTION

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a chromatography column includes a tube, a fit assembly, a first end fitting and a second end fitting. The tube includes an annular first end face circumscribing a first tube opening, an annular second end face circumscribing a second tube opening, an axial bore in fluid communication with the first tube opening and the second tube opening, and an annular protrusion extending axially from the first end face to an axial protrusion height and having an inner diameter greater than an inner diameter of the axial bore. The annular protrusion circumscribes a chamber in fluid communication with the axial bore at the first tube opening. The fit assembly includes a first fit and a ring surrounding the first fit, wherein the fit assembly has a frit opening having an inner diameter less than the inner diameter of the annular protrusion. The ring has an outer diameter greater than an outer diameter of the annular protrusion, and a yield strength less than a yield strength of the annular protrusion, the ring contacting the annular protrusion. The first fit and a portion of the ring less than the inner diameter of the chamber cooperatively define a chamber boundary axially opposite to the first end face. The chamber has an axial chamber height extending from the first end face to the chamber boundary. The first end fitting is securely fastened to the tube and includes a frit retaining surface contacting the ring, wherein the ring is axially compressed between the frit retaining surface and the annular protrusion, the ring is deformed around the annular protrusion, and the chamber height is reduced to less than the protrusion height. A second frit may be disposed in fluid communication with the second tube opening. The second end fitting, in which the second frit is disposed, may be securely fastened to the tube.

According to another implementation, a method is provided for assembling a chromatography column. A tube of the chromatography column is filled with a particulate packing material via a first opening of the column while preventing the particulate packing material from escaping through an axially opposite second opening of the column. The tube has an axial bore extending between a first end face and a second end face of the tube, and a chamber circumscribed by an annular protrusion extending axially from the first end face to an axial protrusion height. The annular protrusion has an inner diameter greater than an inner diameter of the axial bore. Both the axial bore and the chamber are filled. A ring of a fit assembly is placed into contact with the annular protrusion wherein the chamber has an axial chamber height initially equal to the protrusion height. The ring has an outer diameter greater than an outer diameter of the annular protrusion, and surrounds a first fit of the fit assembly wherein the fit assembly has a frit opening having an inner diameter less than the inner diameter of the annular protrusion. The packing material is compressed by axially moving a first end fitting into contact with the frit assembly and into secure engagement with the tube, wherein the ring becomes axially compressed between the first end fitting and the annular protrusion, and the ring deforms around the annular protrusion such that the annular protrusion extends into a thickness of the ring, and the chamber height is reduced to less than the protrusion height. A second fit may be installed at the second opening. A second end fitting may be secured to the tube opposite to the first end fitting.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION OF THE INVENTION

Figure 1:
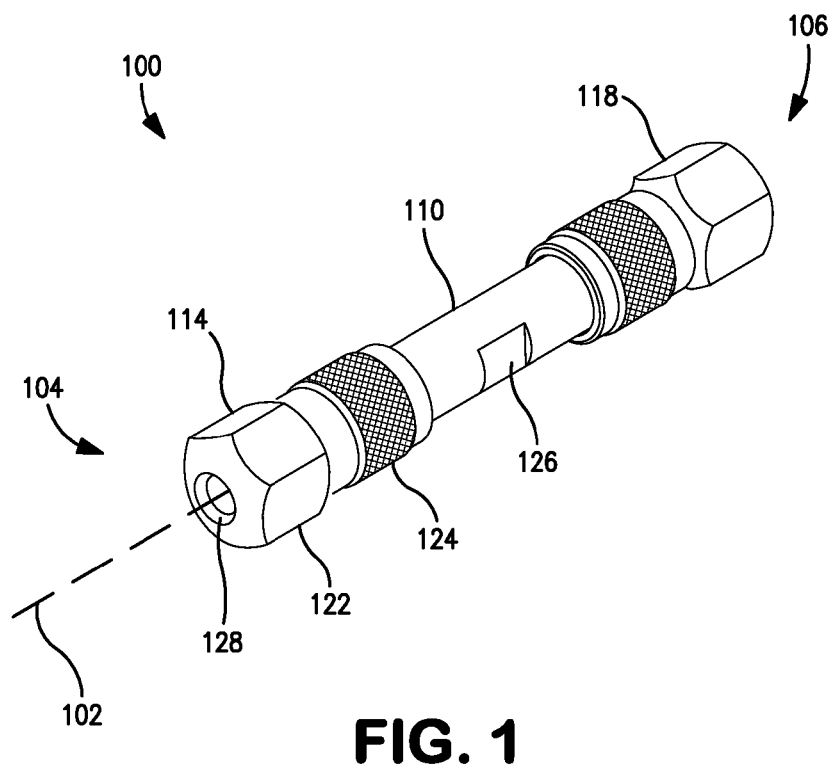
FIG. 1 is a perspective view of an example of a chromatography column according to an implementation of the present disclosure.

FIG. 1 is a perspective view of an example of a chromatography column 100 according to an implementation of the present disclosure. The column 100 generally extends along a longitudinal axis 102 from a first axial end 104 to a second axial end 106. The features of the column 100 may be the same at the first end 104 and the second end 106, in which case the designation of which column end 104 or 106 serves as the inlet end or the outlet end is arbitrary. The column 100 generally includes a tube 110 elongated along the axis 102, a first end fitting 114 securely engaging the tube 110 at the first end 104, and a second end fitting 118 securely engaging the tube 110 at the second end 106. In the present context, "securely engaging" generally means that after the column 100 has been assembled as shown in FIG. 1, the end fittings 114, 118 will not become disengaged from the tube 110 during normal, intended operations of the column 100, including at the pressures typically contemplated for the specific type of chromatography being performed (e.g., HPLC, U(H)PLC, etc.). In the present example, the end fittings 114, 118 may be securely engaged to the tube 110 via the mating of complementary threads (not shown) on inside surfaces of the end fittings 114, 118 and outside surfaces of the tube 110. For this purpose, the end fittings 114, 118 may include flats 122 for manipulation by a tool and/or knurling 124, and the tube 110 may likewise include flats 126. In alternative implementations, the end fittings 114, 118 may be securely engaged to the tube 110 by press-fitting, welding, brazing, etc. Each end fitting 114, 118 includes a bore 128 adapted for connection to the fluid lines of a chromatographic system. For example, the bore 128 may include threads for engaging a fluid conduit fitting (not shown). Each bore 128 is in fluid communication with an axial bore of the tube 110, whereby a fluid flow path is established from the first (inlet) end 104, through the tube 110 and to the second (outlet) end 106 in a manner appreciated by persons skilled in the art.

Figure 2:
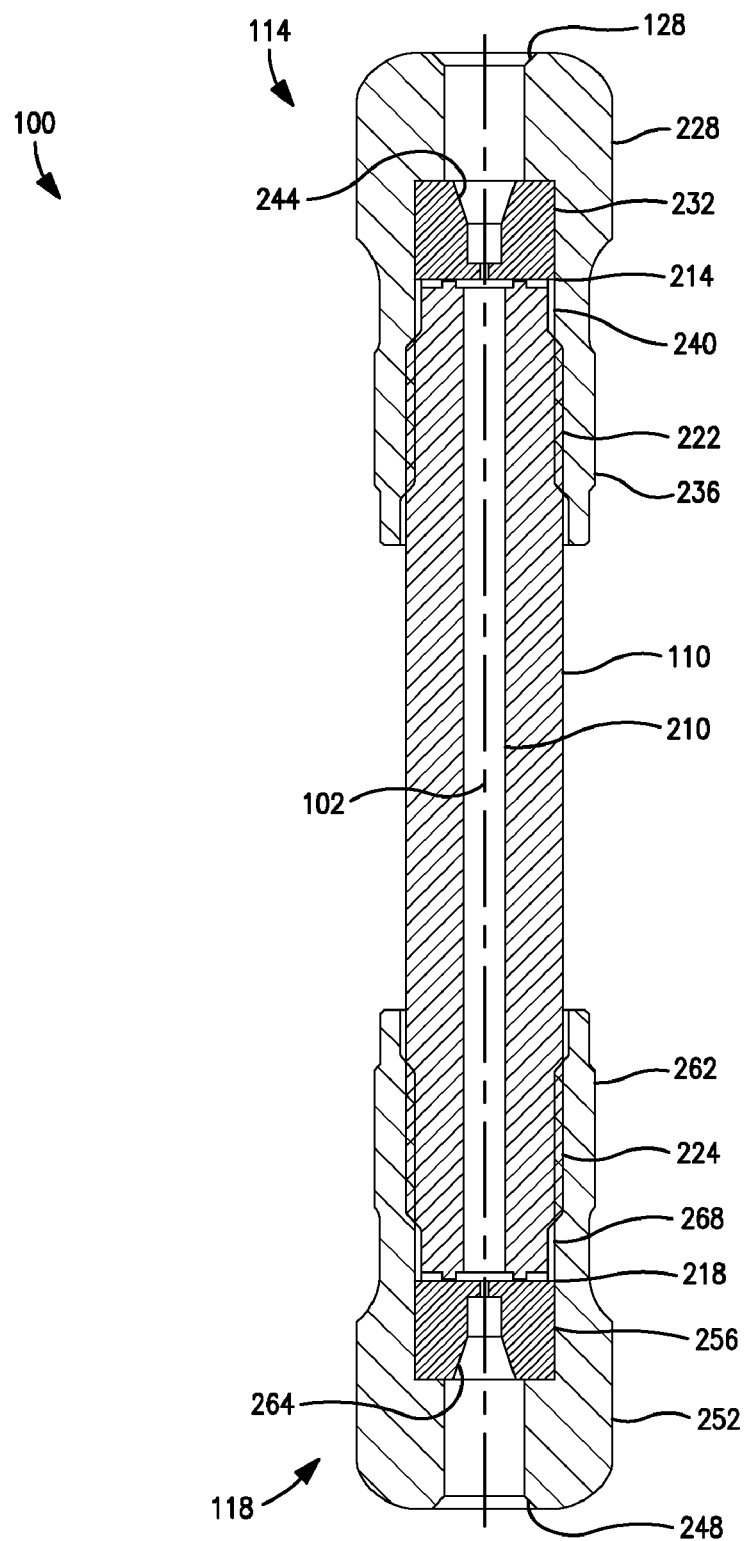
FIG. 2 is a cross-sectional view of the column illustrated in FIG. 1 along a longitudinal axis thereof.

FIG. 2 is a cross-sectional view of the column 100 along the longitudinal axis 102. The tube 110 includes an axial bore 210 extending from one axial end of the tube 110 to the opposite axial end of the tube 110. In the assembled form of the column 100, the axial bore 210 contains (is filled with) a particulate packing material providing the stationary phase for chromatography. Respective fit (or filter) assemblies 214, 218 are positioned at each axial end of the tube 110. The fit assemblies 214, 218 provide axial boundaries holding the particulate packing material in place, yet include central porous sections to enable passage of the mobile phase/sample matrix as appreciated by persons skilled in the art. In the present example, respective threads of the end fittings 114, 118 and the tube 110 form annular threaded areas 222, 224 near the respective axial ends of the tube 110. Also, in the present example, the first end fitting 114 includes an end portion 228 and a frit retainer 232. The end portion 228 and the frit retainer 232 may be physically separate components as in the present example, or alternatively may be integrated as a single-piece construction for the first end fitting 114. The end portion 228 may include a sleeve 236 that coaxially surrounds a portion of the tube 110. The threads of the end fitting associated with the threaded area 222 may be formed on an inside surface of the sleeve 236. The fit retainer 232 is positioned in abutment with the fit assembly 214 in opposition to the axial end of the tube 110. The frit retainer 232 may include a sleeve 240 that coaxially surrounds the axial end of the tube 110. The frit retainer 232 includes a through-bore 244 in fluid communication with the axial bore 210 via the fit assembly 232, thereby fluidly interconnecting the axial bore 210 of the tube 110 and the bore 128 of the end fitting 114. The end portion 228 may coaxially surround the fit retainer 232, with an inside surface of the end portion 228 abutting the frit retainer 232 in opposition to the fit assembly 214.

Assuming the first end fitting 114 is associated with the fluid inlet of the column 100, the fluid path through the assembled column 100 runs through the bore 128 of the end portion 228 (or through a fluid conduit or fitting connected to the bore 128), the bore 244 of the frit retainer 232, a porous central portion of the first frit assembly 214, the axial bore 210, the second frit assembly 218, and a bore 248 of the second end fitting 118. During assembly of the column 100, axial movement of the end fitting 114 relative to the tube 110 in the direction of the opposing end causes at least a portion of the frit assembly 214 to become axially compressed between the frit retainer 232 and the axial end of the tube 110 in a manner described further below. In the illustrated example, axial movement of the end fitting 114 entails mating the threads at the threaded area 222 and rotating the end portion 228 relative to the tube 110.

It will also be noted in the present example that both the inlet and outlet ends of the column 100 are configured similarly. Accordingly, the second frit assembly 218 may be of similar configuration to the first fit assembly 214, and the second end fitting 118 may include a second end portion 252 with a bore 248 and a sleeve 262 and a second frit retainer 256 with a bore 264 and a sleeve 268. As in the case of the first fit assembly 214, the second frit assembly 218 may be axially compressed after axial movement of the second end fitting 118 relative to the tube 110. Also in this example, the fluid path thus runs from the axial bore 210 through a porous central portion of the second frit assembly 218, the bore 264 of the second frit retainer 256, and the bore 248 of the second end portion 252.

Figure 3:
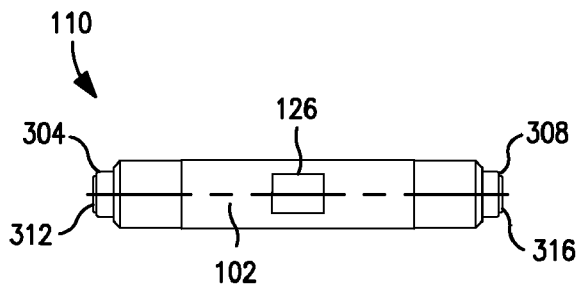
FIG. 3 is a lengthwise view along the longitudinal axis of a tube that may be provided with the column illustrated in FIGS. 1 and 2.
Figure 4:
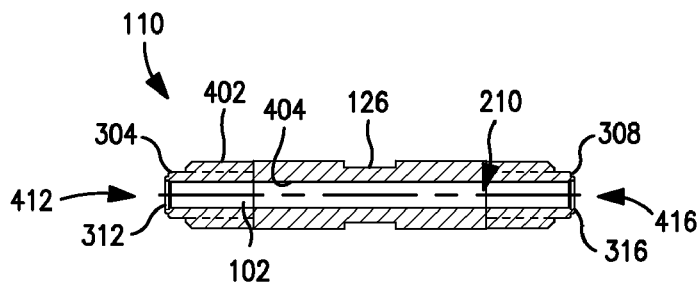
FIG. 4 is a cross-sectional view of the tube illustrated in FIG. 3 along the longitudinal axis.

FIG. 3 is a lengthwise view of the tube 110 along the longitudinal axis 102, and FIG. 4 is a cross-sectional view of the tube 110 along this axis 102. The tube 110 includes a first axial end face 304 and an opposing second axial end face 308. The tube 110 further includes an annular protrusion 312 that extends from the first end face 304 in the axial direction away from the axial bore 210. In the present example in which the ends of the tube 110 are configured similarly, the tube 110 also includes a second annular protrusion 316 that extends from the second end face 308 in the axial direction away from the axial bore 210. Referring to FIG. 4, the tube 110 has an outer surface 402 and an inner surface 404. In the present example, portions of the outer surface 402 include threads (not shown) that mate with threads of the end fittings 114, 118 (FIG. 2). The inner surface 404 circumscribes (defines) the axial bore 210. The axial bore 210 extends between a first opening 412 and a second opening 416 of the tube 110. The first annular protrusion 312 is located at and coaxial with the first tube opening 412, and the second annular protrusion 316 is located at and coaxial with the second tube opening 416. The tube 110 may have any size suitable for the chromatographic application for which the column 100 is intended. As non-limiting examples, the outer diameter of the tube 110 may range from 0.1 mm to 30 mm, and the inner diameter of the tube 110 (the diameter of the axial bore 210) may range from 0.05 mm to 29 mm.

Figure 5:
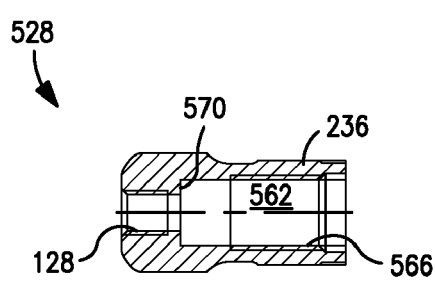
FIG. 5 is a cross-sectional view of an end portion that may be provided with the column illustrated in FIGS. 1 and 2.

FIG. 5 is a cross-sectional view of an end portion 528, which may correspond to the first end portion 228 or the second end portion 252 shown in FIG. 2, or both. In the illustrated example, the bore 128 of the end portion 528 opens into a larger-diameter cavity 562 circumscribed by an inside lateral surface 566 of the sleeve portion 236. The inside diameter of the sleeve portion 236 is larger than the outside diameter of the portion of the tube 110 over which the sleeve portion 236 fits. The bore 128 of the end portion 528 opens at the cavity 562 at an inside axial surface 570. In the illustrated example, a section of an inside lateral surface 566 of the sleeve portion 236 is threaded (not shown) to engage corresponding threads on the outside surface of the tube 110. In the assembled form of the column 100, the sleeve portion 236 encloses the fit retainer 232 and the frit assembly 214, i.e., the fit retainer 232 and the frit assembly 214 are disposed in the cavity 562 of the end portion 528.

Figure 6:
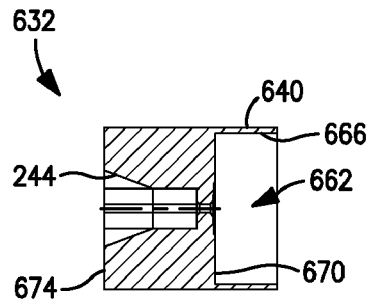
FIG. 6 is a cross-sectional view of a frit retainer that may be provided with the column illustrated in FIGS. 1 and 2.

FIG. 6 is a cross-sectional view of a frit retainer 632, which may correspond to the first frit retainer 232 or the second frit retainer 256 shown in FIG. 2, or both. The bore 244 of the fit retainer 632 may have one or more sections of different diameter, such as tapered sections and/or sections creating stepwise changes in area, as necessary for providing leak-free fluid connections at the end fitting. In the illustrated example, the frit retainer 632 includes a sleeve portion 640 circumscribing a cavity 662. The inside diameter of the sleeve portion 640 is larger than the outside diameter of the portion of the tube 110 over which the sleeve portion 640 fits. The bore 244 of the frit retainer 632 opens at the cavity 662 at a frit retaining surface 670. During assembly of the column 100, the inside axial surface 570 of the end portion 528 (FIG. 5) bears against an axial surface 674 of the frit retainer 632 opposite to the fit retaining surface 670 and, in turn, the fit retaining surface 670 bears against the frit assembly 214 (FIG. 2) on a side of the fit assembly 214 opposite to the annular protrusion 312 (FIG. 3).

Figure 7:
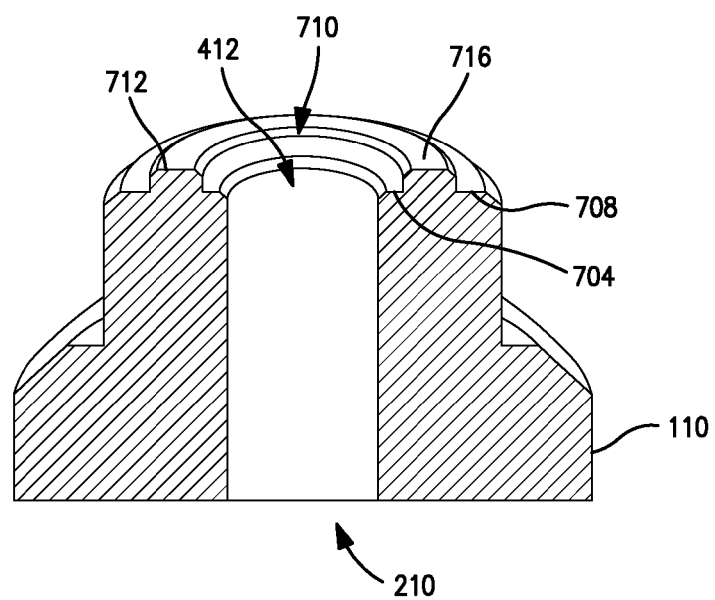
FIG. 7 is a perspective view in cross-section of one axial end of the tube illustrated in FIGS. 3 and 4.

FIG. 7 is a perspective view in axial cross-section of one axial end of the tube 110. The illustrated end may be the inlet end or the outlet end of the tube 110, or may be representative of both ends. FIG. 7 illustrates more clearly the annular protrusion 712 that extends from the axial end face of the tube 110 at the tube opening 412. The inside diameter of the annular protrusion 712 is greater than the inside diameter of the axial bore 210, and the outside diameter of the annular protrusion 712 is less than the outside diameter of the outer surface of the tube 110 at this location. Consequently, the annular protrusion 712 partitions the axial end face into an inner end face portion 704 circumscribing the tube opening 412 and an outer end face portion 708 coaxial with the inner end face portion 704. Moreover, the annular protrusion 712 circumscribes a chamber 710 positioned in fluid communication with the axial bore 210 via the tube opening 412. It can be seen that the chamber 710 is bounded at one axial end by the inner end face portion 704, at the opposing axial end by the fit assembly 214 (FIG. 2), and in the radial direction by the inner surface (inside diameter) of the annular protrusion 712. As described further below, during assembly both the chamber 710 and the axial bore 210 are filled with the particulate packing material.

The annular protrusion 712 extends from the axial end face 704, 708 to a fixed axial protrusion height defined between the axial end face 704, 708 and an opposing axial end surface 716 of the annular protrusion 712 (or to a point or apex of the annular protrusion 712, depending on its shape). It thus can be seen that when the fit assembly 214 is placed in contact with the annular protrusion 712 (i.e., into abutment with its axial end surface 716), the portion of the frit assembly 214 coextensive with the inside diameter of the annular protrusion 712 serves as an upper chamber boundary, the term "upper" being descriptive solely from the perspective of FIG. 7. At this position and prior to compression of the fit assembly 214, the axial height of the chamber 710 is equal to the protrusion height. In the present context, the term "equal" is intended to encompass the term "substantially equal" to take into account an implementation in which the surface of the fit assembly 214 bounding the chamber 710 may not be perfectly flat or planar.

As described further below, the axial compressive forces imparted during assembly of the column 100 cause a portion of the frit assembly 214 to become deformed around the annular protrusion 712. From the perspective of FIG. 7, this compression has the effect of "lowering" the upper chamber boundary presented by the fit assembly 214 toward the tube opening 412. Stated differently, after compression the axial chamber height is reduced to a value less than the fixed protrusion height. Hence, the chamber boundary may be characterized as being axially movable (or variable, or adjustable) from a first position at which the chamber height is at a maximum or initial value (equal to the protrusion height) to a second or final position at which the chamber height is a reduced chamber height. Likewise the chamber volume, defined by the variable chamber height and the fixed inside diameter of the annular protrusion 712, is also reduced from a maximum value at the first position to a reduced value at the second position. The chamber 710 provides an additional space into which particulate packing material is filled during assembly. During assembly, the axial movement of the movable chamber boundary (in consequence of the axial movement of the end fitting 114 into secure engagement with the tube 110) compresses the particulate packing material residing in the chamber 710, whereby at least some of the packing material in the chamber 710 is forced into the axial bore 210. This ensures that the packing material provided with the finally assembled column 100 is at a density and stability desired for that particular column 100.

As also illustrated in FIG. 7, the annular protrusion 712 may be shaped or profiled in a manner that promotes deformation of the frit assembly 214. Thus, in the illustrated example, the annular protrusion 712 includes chamfered edges. Alternatively, the annular protrusion 712 may have a rounded or domed profile. Stated in another way, the annular protrusion 712 may be shaped so as to facilitate extension or excursion of the annular protrusion 712 into the thickness of the deformable portion of the fit assembly 214.

Figure 8:
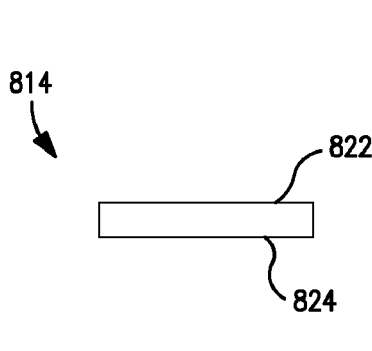
FIG. 8 is a side view of an example of a frit assembly that may be provided with the column illustrated in FIGS. 1 and 2.
Figure 9:
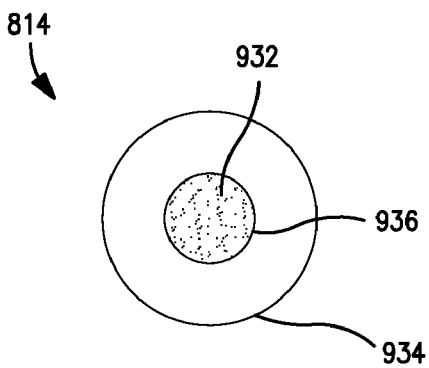
FIG. 9 is a plan view of the frit assembly illustrated in FIG. 8.

FIG. 8 is a side view of an example of a fit (or filter) assembly 814, which may correspond to the first fit assembly 214 or the second fit assembly 218 shown in FIG. 2, or both. FIG. 9 is a plan view of the same fit assembly 814. Referring to FIG. 8, the fit assembly 814 generally includes a first axial surface 822 and an opposing second axial surface 824. In the assembled form of the column 100, the fit assembly 814 is axially interposed between the fit retainer 232 and corresponding axial end of the tube 110 (FIG. 2). Thus, for example, the first axial surface 822 may contact the fit retaining surface 670 (FIG. 6) and the second axial surface 824 may contact the annular protrusion 712 (FIG. 7).

Referring to FIG. 9, the frit assembly 814 includes a frit 932 encapsulated or surrounded by a deformable material. The fit assembly 814 is fabricated such that the deformable material has the form of a ring 934 that circumscribes a central fit opening 936 through which the frit 932 spans. It will be understood that while in the example of FIG. 8, each axial surface 822, 824 lies entirely in the same plane such that the axial thickness of the frit assembly 814 is uniform along any radial direction, this is not a limitation of the frit assemblies encompassed by the present disclosure. For instance, the axial thickness of the frit 932 may be greater or less than the axial thickness of the ring 934 that encloses the frit 932. Generally, no specific limitation is placed on the manner of fabricating the fit assembly 814; the chosen technique will depend on factors such as the materials utilized for the frit 932 and the ring 934. The fit 932 may be composed of any mesh or porous material suitable for use in chromatographic columns. The mesh size or porosity of the frit 932 is sufficient to retain the particulate packing material in the tube 110. Examples of the fit material include, but are not limited to, various metals and metal alloys such as sintered steel, stainless steel, etc., ceramics such as titanium dioxide, polymers such as PEEK (polyaryletheretherketone), etc.

The ring 934 may be composed of any suitable deformable material. In the present context, a "deformable material" is one that enables the ring 934 to deform around the annular protrusion 712 during assembly of the column 100, to a degree sufficient to reduce the chamber height and compress the packing bed in accordance with the teachings disclosed herein. In some implementations, the "deformable material" of the ring 934 may be characterized as being weak in comparison to the material of the annular protrusion 712—that is, the ring 934 is composed of a weak material while the annular protrusion 712 is composed of a hard material. In some implementations, a "weak" material may be characterized as one having a yield strength (or tensile strength) less than 200 MPa, while a "hard" material may be characterized as one having a yield strength of 200 MPa or greater. Accordingly, in some implementations the ring 934 may be composed of a material having a yield strength less than 200 MPa and the annular protrusion 712 may be composed of a material having a yield strength of 200 MPa or greater. Non-limiting examples of the ring material include, but are not limited to, PEEK, Teflon® (polytetrafluoroethylene), etc. As a further example, depending on the formulation of PEEK selected, the yield strength of a PEEK ring 934 may range from about 89.6-140 MPa. Non-limiting examples of the material of the annular protrusion 712 include, but are not limited to, various metals and metal alloys such as titanium, stainless steel, etc., various glasses, and various hard polymers (i.e., polymers having a yield strength of 200 MPa or greater). In other examples, the ring 934 has a yield strength ranging from 40 to 199 MPa and the annular protrusion 712 has a yield strength ranging from 400 to 2000 MPa.

The diameter of the central fit opening 936 (the inside diameter of the ring 934) is less than the inside diameter of the annular protrusion 712 (FIG. 7), while the outside diameter of the ring 934 is greater than the outside diameter of the annular protrusion 712. By way of example and not by limitation, the ring 934 may have an inside diameter of about 2.4 mm, an outside diameter of about 5.45 mm, and a thickness of about 0.8 mm. During assembly of the column 100, the fit assembly 814 is centered on the annular protrusion 712 such that central fit opening 936 is aligned with the chamber 710 and the tube opening 412 along the central axis of the tube 110 while the deformable ring 934 is brought into contact with the axial surface 716 of the annular protrusion 712. The solid, deformable portion of the ring 934 may be characterized as having a lateral width (in the horizontal direction from the perspective of FIGS. 8 and 9) defined as the difference in the radii of the outer sidewall and inner sidewall of the ring 934 (or the difference in the outer and inner diameters of the ring 934, divided by 2). The annular protrusion 712 may likewise be characterized as having a lateral width defined as the difference in the radii of the outer sidewall and inner sidewall of the annular protrusion 712. The lateral width of the ring 934 is greater than the lateral width of the annular protrusion 712. The lateral width of the ring 934 is large enough to ensure that a sufficient amount of the ring material deforms around the outer surfaces of the annular protrusion 712, to result in a sufficient reduction in chamber height and consequent compression of the packing bed. In some implementations, the ring material is deformed to a degree that the ring is in compressive contact with the axial end face 704, 708 of the tube 110 or at least with the outer section 708 thereof (FIG. 7).

Figure 10:
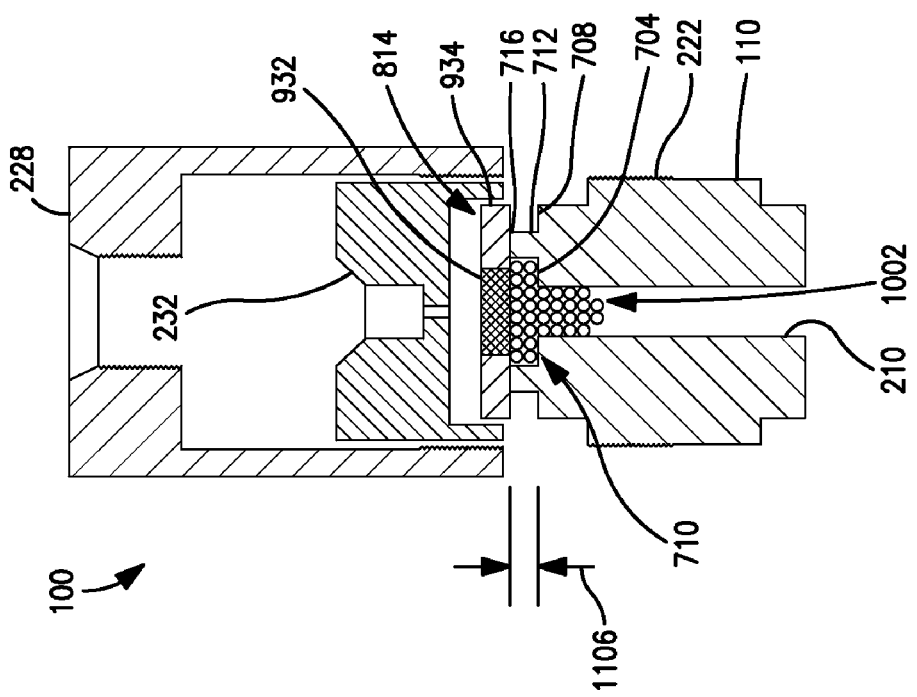
FIG. 10 is a cross-sectional view along the longitudinal axis of an end section of the column illustrated in FIGS. 1 and 2, wherein the column is unassembled.

FIG. 10 is a cross-sectional view along the longitudinal axis of an end section of the column 100 in unassembled form, but after the axial bore 210 and the chamber 710 have been filled with a packing material 1002 (only partially shown for simplicity) and the frit assembly 814 has been placed in contact with the annular protrusion 712 provided at this end of the tube 110. For descriptive purposes, the arrangement of the column 100 illustrated in FIG. 10 will be referred to as the first position of the column 100. As noted above, the chamber 710 is in open communication with the axial bore 210 of the tube 110. The chamber 710 is bounded in the radial direction by the inner wall of the annular protrusion 712 corresponding to its inside diameter, and in the axial direction by the inner section 704 of the axial end face of the tube 110 within the inside diameter of the annular protrusion 712 and by the axially opposing chamber boundary. The chamber boundary is defined by that portion of the side the frit assembly 814 facing the chamber 710 and within the inside diameter of the annular protrusion 712. In other words, the chamber boundary includes the frit 932 and the portion of the deformable ring 934 within the inside diameter of the annular protrusion 712. At the first position, the axial height of the chamber 710 is at a maximum chamber height 1006.

Figure 11:
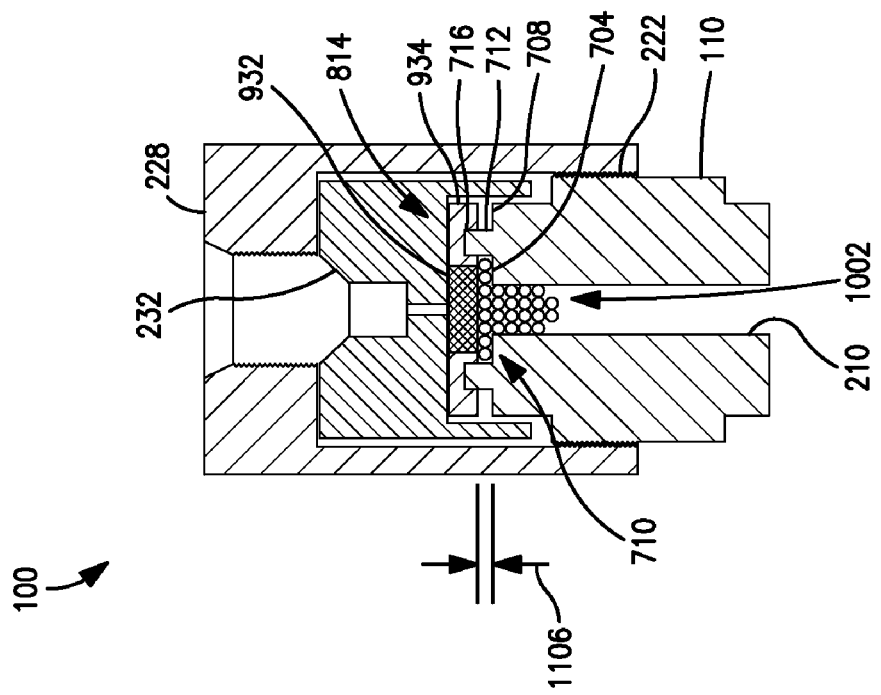
FIG. 11 is a cross-sectional view along the longitudinal axis of column end section illustrated in FIG. 10, wherein the column is assembled.

In comparison to FIG. 10, FIG. 11 is a cross-sectional view of the same column end section but after the column 100 has been assembled. For descriptive purposes, the finally assembled form of the column 100 illustrated in FIG. 11 will be referred to as the second position of the column 100. At the second position, an end fitting has been securely engaged to the tube 110. In the illustrated example, the end fitting includes the end portion 228 and frit retainer 232 described earlier in this disclosure, and secure engagement/assembly is as follows. The frit retainer 232 is positioned onto the frit assembly 814 and the end portion 228 is positioned onto the frit retainer 232 in the manner described earlier. In the present example, the positioning of the end portion 228 entails mating threads of the end portion 228 with threads of the tube 110 at a threaded area 222 of a desired axial length. The end portion 228 is then moved or translated in the axial direction toward the tube 110 (downward from the perspective of FIG. 11), which in the present example entails screwing the end portion 228 onto the tube 110 via the threaded engagement along the threaded area 222. The axial movement of the end portion 228 relative to tube 110 causes the end portion 228 to bear against the frit retainer 232 and, in turn, the frit retainer 232 to bear against the frit assembly 814. Consequently, the frit assembly 814 becomes axially compressed between the frit retainer 232 and the annular protrusion 712.

As a further consequence of assembling the column 100, because the ring 934 of the frit assembly 814 is deformable and significantly weaker (more yielding) than the annular protrusion 712, the ring 934 becomes deformed around the axial surface 716 and inner and outer sidewalls of the annular protrusion 712, in a sense enabling the annular protrusion 712 to extend into the thickness of the ring 934. Due to the yielding of the ring 934, the axial translation and compression cause the chamber boundary presented by the frit assembly 814 to likewise move in the direction of the axial bore 210, whereby the height of the chamber is lowered from the maximum chamber height 1006 associated with the first position (FIG. 10) to a reduced chamber height 1106. Because both the chamber 710 and the axial bore 210 are filled with the packing material 1002, the packing material 1002 likewise becomes compressed to a density desired for the column 100. Moreover, any voids or dead spaces that may have formed in the packing material 1002 during or after the filling process are eliminated.

An example of assembling the column 100 will now be described with reference primarily to FIGS. 2, 10 and 11. One end of the column 100 (e.g., the outlet end) is connected to a frit assembly 814 and corresponding end fitting (in the present example, a frit retainer 232 and end portion 228) in a manner that holds the frit assembly 814 in place but does not reduce the chamber 710, i.e., similar to the "first position" illustrated in FIG. 10. This ensures that the maximum volume of the chamber 710 at this end is available for filling with the packing material 1002 and thus a maximum amount of compression is subsequently available. The other end of the column 100 (e.g., the inlet end) is then connected to a packing reservoir at a packing station (not shown) in a manner known to persons skilled in the art. For instance, this end of the column 100 may be screwed into an adapter of the packing reservoir in a sealed manner. At this end, a frit assembly 814 is not yet installed because the packing material 1002 needs to pass into the column 100 from the packing reservoir. The packing reservoir is filled with the packing material 1002, typically in the form of suspension or slurry with a suitable fluid (which may have a standard mobile-phase composition). A high-pressure pump connected to the packing reservoir is then operated to push a fluid (e.g., pumping solvent) through the packing reservoir and the column 100 and out the opposite, open end of the column 100, after which the pumping fluid may be collected. The pumping operation pushes packing material 1002 from the packing reservoir into the column 100, thereby filling the axial bore 210 and the chamber 710 with the packing material 1002 (or filling both chambers 710 at both column ends in the present embodiment in which both ends are configured with the chambers 710 taught herein). The frit assembly 814 located that the column end opposite to the packing reservoir prevents the packing material 1002 from escaping the column 100 while permitting the pumping fluid to pass therethrough. During the filling process, the particles of the packing material 1002 become arranged into a dense packing bed in the column 100. Generally, higher pressures and higher flow rates of the pumping fluid will result in a denser packing bed.

After the column 100 (axial bore 210 and chamber(s) 710) have been completely filled with the packing material 1002, a valve between the pump and the packing reservoir is closed. The flow of pumping fluid stops and the system pressure is reduced to the pressure at the column outlet (typically ambient pressure, or about 1 bar). The release of pressure may cause the packing bed residing in the column 100 to relax such that the density (and stability) of the packing bed is reduced to an undesired level. After filling and pressure release, the column 100 is decoupled from the packing reservoir and a second frit assembly 814 and corresponding end fitting (in the present example, a frit retainer 256 and end portion 252) is quickly installed at this column end. The transition from decoupling the column 100 to installing the second frit assembly 814 and end fitting may result in a small loss of packing material 1002 from the column 100, thus also contributing to an undesired lowering of density and attendant reduction in stability of the packing bed.

At this point, each end fitting is then securely engaged to the tube 110 of the column 100, whereby each column end assumes a final, "second position" similar to that illustrated in FIG. 11. The securing of the end fittings entails axial translation, compression and deformation as described above. Accordingly, the chambers 710 are reduced and the packing bed is compressed at both column ends, thereby eliminating any voids or pockets in the packing material 1002 and raising the density of the packing material 1002 to a level desired for that particular column 100. It will be noted that the amount of axial compression of the packing bed (or reduction in chamber height) is predetermined or preset prior to assembly of the column 100. It will also be appreciated that the chamber 710 functions as a built-in packing reservoir internal to the column 100. During the assembly of a column end, as illustrated by the transition from the first position shown in FIG. 10 to the second position shown in FIG. 11, the reduction of the chamber 710 in effect adds particulate material to the packing bed residing in the axial bore 210 of the tube 110. Moreover, the chamber boundary facing the packing bed—i.e., the frit 932 and the portion of the deformable ring 934 within the inside diameter of the annular protrusion 712—axially translates from the first position to the second position and thus may be characterized as being axially movable or adjustable. The axial translation of the chamber boundary compresses the packing bed so as to sufficiently preventing subsequent rearrangement of the particles during use of the column 100. The assembled column 100 is then ready for testing or analytical operation in any suitable chromatography system.

To further illustrate the axial translation, compression and deformation that occurs during assembly, a few non-limiting examples will now be given. In one example, the fixed protrusion height (or maximum chamber height) ranges from 0.1-10 mm. In another example, after compression (e.g., the second position illustrated in FIG. 11) the reduced chamber height ranges from 10-90% of the protrusion height. In another example, the reduced chamber height ranges from 0.01-9 mm. In another example, the axial compression length (e.g., the distance from the maximum chamber height and the reduced chamber height) ranges from 0.01-9 mm.

Columns as disclosed herein may be utilized for any type of chromatographic operation, examples of which include liquid chromatography (LC), high performance liquid chromatography (HPLC), and ultra high performance liquid chromatography (U(H)PLC). The columns thus may have any suitable axial length and diameter and operate at any suitable pressure, e.g., as high as several thousands or tens of thousands of psi (or hundreds of MPa). The particulate packing material utilized in columns as disclosed herein may be any material providing a stationary phase for any type of chromatographic technique. Examples of the packing material include, but are not limited to, silica, polymeric formulations, titanium dioxide, zirconium dioxide, and modifications of the foregoing. No specific limitations are placed on the size, size distribution, or chemical moieties presented by the particles of the packing material. A typical average size of a particle is on the micro-scale and may be less than 3 microns. The columns may be utilized for performing any type of LC technique including, but not limited to, normal-phase, reverse-phase, etc.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A chromatography column, comprising:

a tube comprising an annular first end face circumscribing a first tube opening, an annular second end face circumscribing a second tube opening, an axial bore in fluid communication with the first tube opening and the second tube opening, and an annular protrusion extending axially from the first end face to an axial protrusion height and having an inner diameter greater than an inner diameter of the axial bore, wherein the annular protrusion circumscribes a chamber in fluid communication with the axial bore at the first tube opening;

a fit assembly comprising a first frit and a ring surrounding the first fit wherein the frit assembly has a frit opening having an inner diameter less than the inner diameter of the annular protrusion, the ring having an outer diameter greater than an outer diameter of the annular protrusion and having a yield strength less than a yield strength of the annular protrusion, the ring contacting the annular protrusion, wherein the first frit and a portion of the ring less than the inner diameter of the chamber cooperatively define a chamber boundary axially opposite to the first end face and the chamber has an axial chamber height extending from the first end face to the chamber boundary;

a first end fitting securely fastened to the tube and comprising a fit retaining surface contacting the ring, wherein the ring is axially compressed between the frit retaining surface and the annular protrusion, the ring is deformed around the annular protrusion, and the chamber height is reduced to less than the protrusion height;

a second frit disposed in fluid communication with the second tube opening; and a second end fitting in which the second frit is disposed, the second end fitting securely fastened to the tube.

2. The chromatography column of claim 1, wherein:

the chamber at the first tube opening is a first chamber, the annular protrusion circumscribing the first chamber is a first annular protrusion, the ring surrounding the first frit is a first ring, the frit assembly comprising the first frit and the first ring is a first fit assembly, the frit opening of the first fit assembly is a first frit opening, and the frit retaining surface of the first end fitting is a first fit retaining surface;

the tube further comprises a second annular protrusion extending axially from the second end face to an axial protrusion height and having an inner diameter greater than an inner diameter of the axial bore, wherein the second annular protrusion circumscribes a second chamber in fluid communication with the axial bore at the second tube opening;

the chromatography column further comprises a second frit assembly, the second frit assembly comprising the second frit and a second ring surrounding the second frit wherein the second frit assembly has a second frit opening having an inner diameter less than the inner diameter of the second annular protrusion, the second ring having an outer diameter greater than an outer diameter of the second annular protrusion and having a yield strength less than a yield strength of the second annular protrusion, the second ring contacting the second annular protrusion wherein the second frit and a portion of the second ring less than the inner diameter of the second chamber cooperatively define a second chamber boundary axially opposite to the second end face and the second chamber has an axial chamber height extending from the second end face to the second chamber boundary; and the second end fitting comprises a second frit retaining surface contacting the second ring, wherein the second ring is axially compressed between the second frit retaining surface and the second annular protrusion, the second annular protrusion extends into a thickness of the second ring wherein the second ring is deformed around the second annular protrusion, and the chamber height of the second chamber is less than the protrusion height of the second protrusion.

3. The chromatography column of claim 1, wherein:

the first end fitting is axially movable relative to the tube from a first position to a second position, such that the chamber boundary is axially movable in response to movement of the first end fitting;

at the first position, the chamber has a maximum chamber height equal to the protrusion height; and at the second position, the ring is deformed around the annular protrusion and the chamber height is a reduced chamber height less than the protrusion height.

4. The chromatography column of claim 3, further comprising a particulate packing material filling the axial bore and the chamber, wherein at the first position the particulate packing material has a first volume, and at the second position the particulate packing material has a second volume less than the first volume and particulate packing material is compressed.

5. The chromatography column of claim 3, wherein the chamber boundary is axially movable from the first position to the second position over an axial compression length ranging from 0.01-9 mm.

6. The chromatography column of claim 1, wherein the protrusion height ranges from 0.1-10 mm, and the reduced chamber height ranges from 0.01-9 mm.

7. The chromatography column of claim 1, wherein the chamber height ranges from 10-90% of the protrusion height.

8. The chromatography column of claim 1, further comprising a particulate packing material filling the axial bore and the chamber, wherein the particulate packing material is compressed.

9. The chromatography column of claim 1, wherein the first end face comprises an outer section adjacent to the outer diameter of the annular protrusion, and the outer section is in compressive contact with the ring.

10. The chromatography column of claim 1, wherein the first end fitting is securely fastened to the tube by threads of the first end fitting mating with threads of the tube, and the first end fitting and the chamber boundary are axially movable by rotation of the first end fitting relative to the tube.

11. The chromatography column of claim 1, wherein the ring has a composition selected from the group consisting of polyaryletheretherketone, polytetrafluoroethylene, and materials having a yield strength less than 200 MPa.

12. The chromatography column of claim 1, wherein the annular protrusion has a composition selected from the group consisting of metals, glasses, ceramics, and polymers having a yield strength of 200 MPa or greater.

13. The chromatography column of claim 1, wherein the yield strength of the ring ranges from 40-199 MPa and the yield strength of the annular protrusion ranges from 400-2000 MPa.

* * * * *

UNITED STATES PATENT AND TRADEMARK OFFICE
CERTIFICATE OF CORRECTION

| | | |
|---|---|---|
| PATENT NO. | : 8,147,690 B2 | Page 1 of 1 |
| APPLICATION NO. | : 12/909311 | |
| DATED | : April 3, 2012 | |
| INVENTOR(S) | : von Doehren et al. | |

It is certified that error appears in the above-identified patent and that said Letters Patent is hereby corrected as shown below:

On the Title page, in Item (57), under "Abstract", in column 2, line 1, delete "fit" and insert -- frit --, therefor.

On the Title page, in Item (57), under "Abstract", in column 2, line 6, delete "fit" and insert -- frit --, therefor.

In column 12, line 20, in Claim 1, delete "fit" and insert -- frit --, therefor.

In column 12, line 21, in Claim 1, delete "fit" and insert -- frit --, therefor.

In column 12, line 34, in Claim 1, delete "fit" and insert -- frit --, therefor.

In column 12, line 48, in Claim 2, delete "fit" and insert -- frit --, therefor.

In column 12, line 49, in Claim 2, delete "fit" and insert -- frit --, therefor.

In column 12, line 50, in Claim 2, delete "fit" and insert -- frit --, therefor.

Signed and Sealed this
Fifteenth Day of May, 2012

David J. Kappos
*Director of the United States Patent and Trademark Office*